US010751129B2

(12) United States Patent
Robertson (10) Patent No.: US 10,751,129 B2
(45) Date of Patent: Aug. 25, 2020

(54) SYSTEM AND METHOD FOR AUTOMATICALLY GENERATING A FACIAL REMEDIATION DESIGN AND APPLICATION PROTOCOL TO ADDRESS OBSERVABLE FACIAL DEVIATIONS (71) Applicant: John Gordon Robertson, Victoria (CA)

(72) Inventor: John Gordon Robertson, Victoria (CA)

( * ) Notice: Subject to any disclaimer, the term of this patent is extended or adjusted under 35 U.S.C. 154(b) by 0 days.

(21) Appl. No.: 16/221,448

(22) PCT Filed: May 16, 2017

(86) PCT No.: PCT/CA2017/050580
§ 371 (c)(1),
(2) Date: Dec. 18, 2018

(87) PCT Pub. No.: WO2017/219123
PCT Pub. Date: Dec. 28, 2017

(65) Prior Publication Data
US 2019/0254748 A1 Aug. 22, 2019

(30) Foreign Application Priority Data

Jun. 21, 2016 (CA) ...................... 2933799

(51) Int. Cl.
| *A61B 34/10* | (2016.01) |
| *A61B 5/00* | (2006.01) |
| *G06T 7/00* | (2017.01) |
| *G06T 11/60* | (2006.01) |
| *G06K 9/00* | (2006.01) |
| *G06F 3/0482* | (2013.01) |

(52) U.S. Cl.
CPC ............ *A61B 34/10* (2016.02); *A61B 5/0077* (2013.01); *G06K 9/00281* (2013.01); *G06T 7/0014* (2013.01); *G06T 11/60* (2013.01); *A61B 2034/105* (2016.02); *G06F 3/0482* (2013.01); *G06T 2200/24* (2013.01); *G06T 2207/30201* (2013.01)

(58) Field of Classification Search
CPC combination set(s) only.
See application file for complete search history.

(56) References Cited

U.S. PATENT DOCUMENTS

| 2015/0278997 | A1* | 10/2015 | Kim | ................... | G06K 9/00281 382/195 |
| 2015/0310673 | A1* | 10/2015 | Romdhani | ......... | G06K 9/00275 345/420 |
| 2019/0313915 | A1* | 10/2019 | Tzvieli | ................... | A61B 5/015 |

* cited by examiner

*Primary Examiner* — Wesner Sajous
(74) *Attorney, Agent, or Firm* — Klarquist Sparkman, LLP (57) ABSTRACT Described are various embodiments of a computerized method and system for automatically developing a facial remediation protocol for a user based on an input facial image of the user, wherein facial remediation design or plan comprises a combination of one or more of a surgical plan to shift or change the size of various facial anatomical features, a makeup plan to change the apparent size or apparent position of various facial anatomical features and other techniques, such as hair design, to reduce the actual and perceived difference between the subject's face and a standard face, for example.

24 Claims, 3 Drawing Sheets

SYSTEM AND METHOD FOR AUTOMATICALLY GENERATING A FACIAL REMEDIATION DESIGN AND APPLICATION PROTOCOL TO ADDRESS OBSERVABLE FACIAL DEVIATIONS

FIELD OF THE DISCLOSURE

The present disclosure relates to facial aesthetic improvement systems and methods, and, in particular, to a system and method for automatically generating a facial remediation design and application protocol to address observable facial deviations.

BACKGROUND

Plastic surgery, makeup, and other aesthetic procedures have been in common use in various parts of the world by individuals seeking to improve their facial appearance, for example, to address certain less desirable facial features that may result from basic aesthetic, ethnic and/or cultural preferences, to more significant features that may have been the result of an accident or injury, or various congenital facial malformations, to name a few examples. Invasive facial reconstructive or structural alternation procedures are not uncommon, particularly for the latter, and can provide some drastic improvements, but often fall short of a truly satisfying result. As such, individuals routinely turn to plastic surgeons, makeup artists or the like to devise a personalized facial remediation plan by hand. These plans generally rely on certain unproven theories or ideas, and mostly rely on a subjective assessment as to how best to enhance the subject's facial appearance.

Recent academic research into the nature and determinants of beauty now provide a much firmer basis upon which to assess a person's facial appearance. For example, the publication "Facial attractiveness: evolutionary based research" by A. C. Little et al. (Phil. Trans. R. Soc. B (2011) 366, 1638-1659) provides a comprehensive overview of current research on the determinants of facial attractiveness. The commercial implications of such research, however, remain particularly limited.

In recent years, a number of computer applications for desktop computers and mobile devices have become available commercially that can be used to capture a facial image and digitally apply/overlay different makeup styles to the facial image. A user can thus preview how they may look if they choose a particular makeup style. These applications, however, provide little guidance or utility beyond the output of layered facial image renderings of a user's facial image and applied makeup style selection.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

A need exists for a system and method for automatically generating a facial remediation design and application protocol, for instance to address facial deviations, that overcome some of the drawbacks of known techniques, or at least, provides a useful alternative thereto. Some aspects of this disclosure provide examples of such systems and methods.

In accordance with one aspect, there is provided a computerized method for automatically developing a facial remediation protocol for a user based on an input facial image of the user, the method comprising: defining a digital user facial structure of the user based on the input facial image; retrieving a designated digital standard facial structure from accessible data storage; computing structural deviations between said digital user facial structure and said designated standard facial structure; retrieving preset digital facial remediation protocol fixes corresponding to at least some of said computed deviations from said accessible data storage, wherein said one or more preset facial remediation protocol fixes have been pre-established to at least partially reduce a visual appearance of corresponding structural deviations; and outputting a digital remediation protocol according to said preset digital makeup protocol fixes.

In one embodiment, defining said digital user facial structure comprises automatically identifying a user set of preset structural landmarks from the input facial image and defining a digital user landmark representation thereof; said designated digital standard facial structure comprises a corresponding standard landmark representation of a corresponding standard set of preset structural landmarks; and said computing comprises computing deviations between said user landmark representation and said standard landmark representation.

In one embodiment the user landmark representation is defined by a user vector of constituent user landmark ratios, and the standard landmark representation is defined by a standard vector of constituent standard landmark ratios.

In one embodiment, the deviations are represented by a deviation vector. In one such embodiment, the deviations are further represented by an asymmetry vector representative of computed asymmetries identified from said user facial structure.

In one embodiment, the structural deviations are automatically ordered, and the preset digital makeup protocol fixes are retrieved so as to address a highest ordered subset of said deviations.

In one embodiment, the standard facial structure is selectable to correspond with one or more user demographical characteristics.

In one embodiment, the one or more user demographical characteristics include at least one of a user age, a user age range, a user ethnicity, and a user gender.

In one embodiment, the standard facial structure is defined as a function of a set of sample facial images of individuals satisfying said one or more demographical characteristics.

In one embodiment, the standard facial structure is defined as a function of an average representation of one or more standard landmarks extracted from each of said set of sample images.

In one embodiment, the facial structure is defined as a function of an attractiveness rating associated with each of said set of sample facial images.

In one embodiment, the method further comprises receiving as input a selectable audience, wherein an audience-specific weighing is applied against said one or more standard landmarks in defining an audience-specific standard facial structure to preferentially appeal to said selected audience.

In one embodiment, the outputting comprises digitally enhancing the facial image to apply said digital facial remediation protocol thereto and output an enhanced digital image representative thereof.

In one embodiment, the enhanced digital image includes an ordered set of enhanced digital images illustrating a progressive application of said digital facial remediation protocol.

In one embodiment, the outputting comprises ordered written instruction for implementing said digital facial remediation protocol.

In one embodiment, an intensity of said digital facial remediation protocol is adjustable so to output a progressive implementation of said facial remediation protocol.

In one embodiment, the image is one of a 2D image and a 3D image.

In one embodiment, the facial remediation protocol consists of a makeup application protocol.

In accordance with another aspect, there is provided a computer-readable medium having statements and instructions stored therein for implementation by a hardware processor to implement the steps of any one of methods noted above.

In accordance with another aspect, there is provided a computerized system for automatically developing a facial remediation protocol for a user based on an input facial image of the user, the system comprising: an image input interface; a facial remediation protocol output interface; a hardware processor; and a data storage device having stored thereon statements and instructions for execution by said hardware processor to implement the steps of any one of above noted methods.

In accordance with another aspect, there is provided a computerized system for automatically developing a facial remediation protocol for a user based on an input facial image of the user, the system comprising: an image input interface; a facial remediation protocol output interface; a hardware processor; and a data storage device having stored thereon: a set of selectable digital standard facial structures; a set of preset digital facial remediation protocol fixes pre-established to at least partially adjust a visual appearance of corresponding facial landmarks or representations thereof; and statements and instructions for execution by said hardware processor to: define a digital user facial structure of the user based on the input facial image received as said image input interface; retrieve a designated one of said selectable standard facial structures; compute structural deviations between said digital user facial structure and said designated one of said standard facial structures; compile a subset of said set of preset digital facial remediation protocol fixes corresponding to at least some of said computed deviations as an output digital makeup protocol; and output said digital facial remediation protocol to said output interface.

In one embodiment, the system further comprises an image capture device operatively coupled to said input interface.

In one embodiment, the input interface and said output interface each comprise a network accessible interface, wherein the user image is uploadable to system via said input interface and said make protocol is retrievable from said output interface over a communication network.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

DETAILED DESCRIPTION

The systems and methods described herein provide, in accordance with different embodiments, different examples in which an automated or semi-automated system can be used to generate a facial remediation design and application protocol for a given user in order to address observable facial deviations. For example, structural deviations may be automatically identified from one or more images of the user's face in comparison with one or more fixed or customizable idealized structural facial models. Generally, facial structures will be defined as a set of characteristics of a face that are independent of scale and skin condition, but rather dependent inter landmark distance ratios, asymmetries, and like relative structural considerations. As detailed below, an output facial remediation design or plan will include a combination of one or more of a surgical plan or protocol to shift or change the size of various facial anatomical features, a makeup plan or protocol to change the apparent size or apparent position of various facial anatomical features and other techniques, such as hair design, to reduce the actual and perceived difference between the subject's face and a standard face, for example.

In some embodiments, the user's age, gender, ethnicity, personal preferences and/or statistically consolidated intended or preferred audience preferences, and like parameters, may be taken into account in order to define an appropriate idealized structural model appropriate and/or realistically targetable for the user. The user's actual and automatically characterized facial structure(s) may then be compared against this model to identify perceivable structural deviations that may be addressed or at least alleviated by the implementation of an automatically generated remediation design and application protocol particular to the user's unique set of structural deviations and idealized structural model. Namely, upon executing the output remediation design and application protocol, the visual appearance of the identified user facial deviations may be significantly reduced, thus allowing the user to partake in day-to-day activities with greater confidence and reduced self-consciousness, for example.

Unlike current makeup style visualization applications, the embodiments considered herein are configured to specifically and automatically account for each user's particular structures and how these structures deviate from an idealized facial structural model, be it one or more selectable standard idealized structural models or a selectable and/or customizable idealized structural model based on various user preferences, characteristics, goals or the like. In doing so, the system can automatically account for these structural deviations and render an appropriate makeup design and application protocol that has a greater likelihood of reducing the appearance of such deviations and thus positively improving the user's appearance, both as perceived by themselves and by others, based on proven and reproducible facial beauty and/or aesthetic factors and characteristics and driven by the stored idealized facial structure models of interest.

Figure 1:
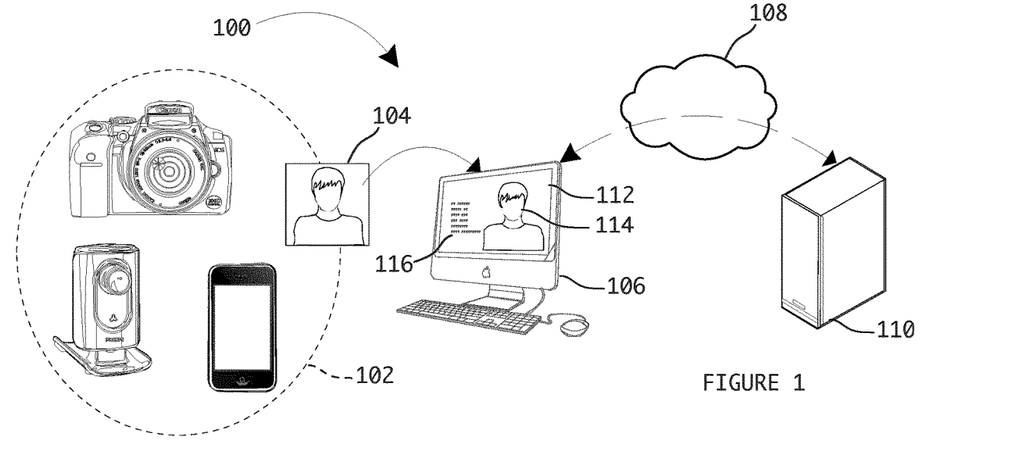
FIG. 1 is a high level diagram of a system for automatically generating a facial remediation design and application protocol to address facial deviations, in accordance with one embodiment.

With reference now to FIG. 1, and in accordance with one embodiment, a system 100 for automatically generating a facial remediation design and application protocol to address facial deviations will now be described. In this embodiment, the system 100 includes, or is executable to interface directly or indirectly with an output of an image capture device 102 that is operable to capture one or more images 104 of a given user's face. Generally, the system will operate best with a front facing image of the user's face, though may equally, additionally or alternatively operate with a profile image or the like, provided various structural features of the user's face can be sufficiently identified and quantified (e.g. landmark position, inter-landmark distance, ratios, etc.) from the image(s) to execute the intended process. A 3D composite image or scan of the user's face may also be considered, as can other facial imaging techniques, as will be readily appreciated by the skilled artisan. For instance, while 2D images are generally considered in the examples provided herein, the system 100 may equally operate to identify and process facial landmark locations from three dimensional images, as might be obtained, for example, from 3D scanners such as computed tomography devices, magnetic resonance image devices, laser surface scanning devices and other 3D scanning devices readily known in the art. The system's output, as will be described in greater detail below, may equally be rendered in 3D so to better illustrate the proposed remediation design and protocol in three dimensions.

In the illustrated example, the image 104 is then locally transferred to a local computing device 106 or the like for initial processing and visualization. Optionally, some of the image and remediation design processing can be offloaded via an appropriate network connection 108 to a remote processing server 110 or the like, as shown, or rather locally processed by the local processing device 106. Processing results are then locally or remotely relayed to a display 112 operatively associated with the local device 106 for visualization by the user in the form of one or more digitally rendered images 114 (e.g. illustrating the proposed remediation design and/or protocol) and/or structured text instructions 116 relaying the steps to execute the proposed remediation protocol.

As will be appreciated by the skilled artisan, different image capture devices 102 may be considered herein to provide similar results, as can different system architectures and intermediary communication/network protocols as may be appropriate. For example, in one embodiment, a stand-alone digital camera can be operated to locally store captured images for subsequent transfer via a wired or wireless port to a local computing device 106 and optional downstream server 110. In a same or alternative embodiment, a Webcam can be used to directly capture and relay user images to the computing device 106 and/or server 110, e.g. within the context of an integrated image capture function forming part of a local, distributed and/or Web-implemented remediation design and protocol processing application. In yet another embodiment, a camera-enabled cellphone, smartphone, or tablet may be used to capture user images for internal storage and processing (e.g. within the context of a self-contained mobile application), and/or to be relayed via an appropriate network connection (e.g. Wi-Fi, cellular data, Bluetooth, etc.) to a local processing device 106 and/or remote server 110. Other system architectures may also be considered, as will be appreciated by the skilled artisan, without departing from the general scope and nature of the present disclosure. For example, a self-contained and/or network-enabled kiosk or the like may be operated within a commercial or clinical setting by professionals and their clients within the context of professional client consultations and the like. Similar embodiments may be implemented within a medical establishment, possibly as a self-contained and/or network-assisted application executed within the greater context of an extended medical or surgical treatment practice or the like. These and other such examples will be appreciated to fall within the scope of the present disclosure.

Figure 2:
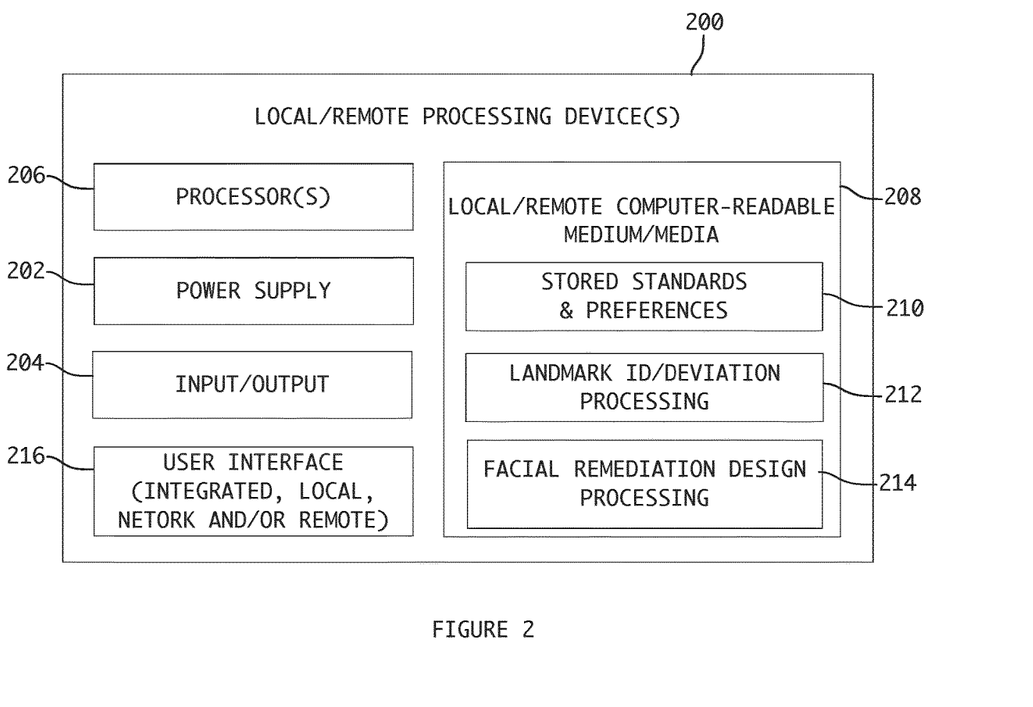
FIG. 2 is a schematic diagram of a processing device for automatically generating a facial remediation design and application protocol to address facial deviations, in accordance with one embodiment.

With added reference to FIG. 2, any of the mobile, local and/or remote processing device(s), alone or in combination (jointly identified as processing device(s) 200 in FIG. 2), will be configured to process the captured image(s) 104 and initiate the automated remediation design and protocol generation process and relay/output the results thereof for visualization by the user. Generally, the processing device(s) will include a power supply 202 and various input/output ports 204 such as an integrated, local and/or remote data input port for receiving as input the one or more images 104 of interest, one or more internal or intermediary communication ports for relaying image, user and processing data between various components of the system, as applicable, and one or more output ports to output the results to the user. An integrated, local, network and/or remote user interface 216 will also generally be provided to allow user execution and operation of the system 100, entry of various user preferences, selections and/or options, and output of various interactive results, as the case may be, to the user. Examples of available user interfaces may include, but are not limited to, a keyboard or wired or wireless keyboard port, a wired or wireless touch pad, a touch screen, a wired or wireless mouse port, track ball and the like, and other such user interfaces readily known in the art.

The processing device 200 will also include one or more integrated, local and/or remote hardware processors 206, such as commonly known in the art, to process the various statements, commands, instructions and inputs of the system in executing the automated makeup design and protocol generation process of interest.

The processing device(s) 200 will also include one or more local and/or remote computer-readable media 208 for storing digital information, instructions and process directives required in the execution of the automated makeup design and protocol generation process. For example, data storage may include one or more databases storing various facial structure standards, preferences and indexes 210, for example, organized and/or inter-related in accordance with various available user-selectable fields and/or options, and/ or again associated with respective preset, evolving and/or customizable standard facial structure types based on ethnicity, gender, age, etc., and/or selectable styles and/or trends based on public facial preference data processing, recognizable celebrity or fashion styles/trends, and the like.

Data storage 208 will also generally include a facial structure analysis module 212 operable to automatically identify particular structural landmarks from the user's image 104, compare them with stored landmark features associated with an idealized facial structure model selected by or for the user, and compute corresponding deviations therefrom in the captured user data. From the processed deviations computed by module 212, an appropriate remediation design and protocol generation module 214 can be invoked to produce the desired results. Further details to this effect will be provided below with reference to the Example described with reference to FIG. 4, below. The output remediation design and protocol can then be relayed for display and implementation.

Figure 3A:
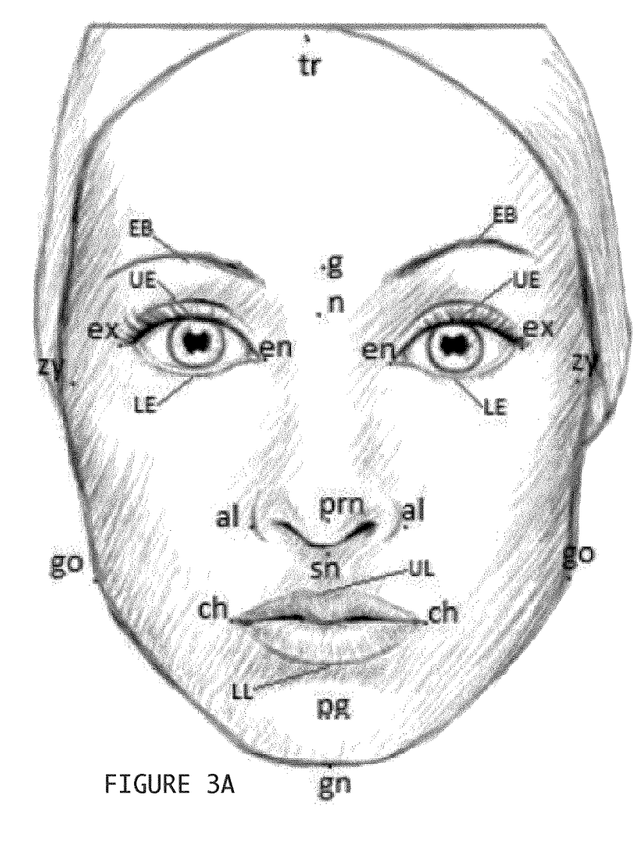
FIGS. 3A and 3B are a sketch and photograph, respectively, of a human face locating various exemplary anatomical landmarks usable in describing a given facial structure, in accordance with one embodiment.
Figure 3B:
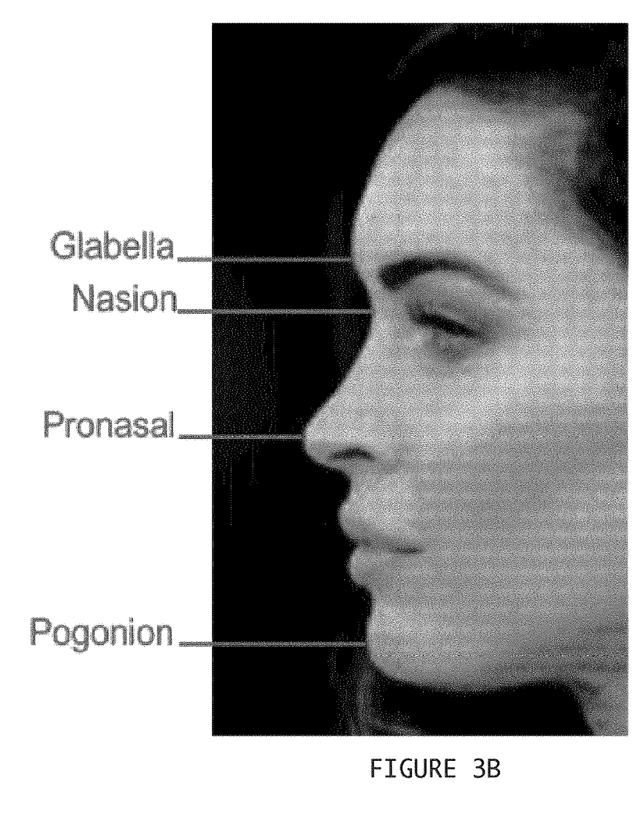

As will be appreciated by the skilled artisan, different facial features and characteristics may be considered in both characterizing the face of the user and that of the multiple facial samples processed to compute the system's various facial Standard structural and Audience preference datasets. The table below provides some examples of observable facial landmarks, as illustrated in FIGS. 3A and 3B, that can, in various combinations, be used to characterize a user's overall facial appearance and deviation from one or more standardized data sets. As will be appreciated by the skilled artisan, while this table outlines various exemplary facial landmarks, namely anatomically identifiable points on the face, that can be used, alone or in combination, to characterize the facial appearance of a user, reference image and/or standard, other landmarks and/or definitions therefor may also be considered without departing from the general scope and nature of the present disclosure.

| Landmark | Abbreviation | Description |
| --- | --- | --- |
| Trichion | Tr | The junction of the hairline and the vertical centre line of the face |
| Eyebrow | Eb | Lower margin of the eyebrow directly above the centre of the pupil |
| Upper eyelid | Ue | The lower margin of the upper eyelid directly above the centre of the pupil |
| Lower eyelid | Le | The upper margin of the lower eyelid directly below the centre of the pupil |
| Exocanthion | Ex | The lateral intersection of the lower and upper eyelids |
| Endocanthion | En | The medial intersection of the upper and lower eyelids |
| Nasion | N | The most posterior point of the nose |
| Pronasal | Prn | The most anterior point of the nose |
| Alare | Al | The most lateral points of the nose |
| Zygoma | Zy | The most lateral point of the zygomatic bone |
| Glabella | G | The intersection of the vertical centre line and the glabella, a ridge just superior to the nasion |
| Gonion | Go | The lowest, posterior, lateral point of the angle of the mandible |
| Subnasal | Sn | The mid-point of the superior margin of the philtrum |
| Upper lip | Ul | The mid-point of the inferior margin of the philtrum |
| Lower Lip | Ll | The midpoint of the lower margin of the inferior lip of the mouth |
| Chelion | Ch | The intersection of the upper margin of the superior lip of the mouth with the lower margin of the inferior lip |
| Gnathion | Gn | The most inferior point of the face |

As noted above, other observable landmarks can also or alternatively be used to produce a like effect, as will be readily appreciated by the skilled artisan, and therefore, the above-listed landmarks should be considered as non-limiting examples, only.

In different embodiments, different combinations of landmark locations (e.g. facial coordinates), distances (e.g. straight-line distance on a facial photograph between any two landmarks), and/or ratios (e.g. the result of dividing a landmark distance of one pair of landmarks by a landmark distance of a second pair of landmarks), may be considered in defining facial appearances and/or deviations. For instance, a standard facial coordinate system may be defined to systematically characterize facial landmarks across users and sampled faces. In one such example, facial coordinates may be defined by a set of orthogonal coordinates with origin such that the value of the vertical coordinate of the Gnathion is zero and the value of the horizontal coordinate of the vertical centre line (the vertical line which divides the face into two mirror halves) is zero and the sum of the absolute values of the deviations of the Trichion, nasion, pronasal and the gnathion plus the absolute values of the sums of the horizontal coordinates of the symmetrical pairs is a minimum. These coordinates may be used alone or in combination with other defining facial features to characterize landmarks, symmetrical pairs (e.g. paired anatomical points that occur on both the left and right sides of the face), and the like.

As noted above in accordance with some embodiments, a face vector may then be defined as a function of these identified landmarks/locations, for example, based on one or more landmark distances and/or ratios represented by a one dimensional vector representative thereof. Other landmark-derived vectors may also or alternatively be defined, such as a horizontal paired asymmetry vector defined by a one dimensional vector whose elements are formed by calculating the ratio of the distance from each symmetrical pair to the vertical centre line, to the distance from the nasion to the Gnathion or another pair of landmarks; a vertical paired asymmetry vector defined by one dimensional vector whose elements are formed by calculating the ratio of the vertical distance between each element of the symmetrical pair, to the distance from the nasion to the Gnathion or another pair of landmarks; and a centre line asymmetry vector defined by a one dimensional vector whose elements are formed by calculating the ratio of the horizontal displacement from the Vertical Centre line of landmarks which should naturally fall on the Vertical Centre Line, to the distance from the nasion to the Gnathion or another pair of landmarks.

Following from the above definitions, and in accordance with one embodiment, a Standard vector can be defined as a one dimensional vector whose elements are the average landmark ratios and/or distances of the members of a given population, which may be selected as a whole, or as a subset from those members of this given population having been associated with a highest ranking by a random sample of ranking individuals or the like. In that context, a given population may be characterized as a standard population, as exemplified below, in which members of this standard population are identified to share a same set of one or more characteristics, such as gender, age group and ethnicity, to name a few examples. Similarly, a standard deviation vector can be defined as a one dimensional vector whose elements are formed by calculating the standard deviations of the elements of the face vectors of those members of the standard population selected to form the standard vector. Other standard population vector definitions may also be considered, as will be appreciated by the skilled artisan, without departing from the general scope and nature of the present disclosure.

As will be described below, based on a selected standard-specific vector and a corresponding user vector, a deviation vector can be defined to represent deviations between the user's facial landmarks and the idealized landmarks defined for the population of interest, which deviations can be used as basis for the establishment of a proposed remediation design and protocol to address or at least partially alleviate some of these deviations.

To further refine or accentuate a particular facial appearance of interest, a number of audience-specific qualifiers may be taken into account so to enhance or promote a desired outcome for a particular target audience. For example, a user may wish to emulate an idealized or averaged highest ranking appearance for a selected standard population which may more or less correspond with their own demographics (e.g. age, gender, ethnicity), while also wishing to enhance this particular idealization for particular facial features and/or landmarks known or predicted to be most attractive or important to a particular audience, namely consisting of individuals sharing certain audience demographics, e.g. young north American males, Korean females in the 30 to 35 age group, etc. Accordingly, an audience vector may also be defined whose elements are formed from the relative importance of each element of the face vectors defined for the standard population of interest. In other words, an intended audience vector may be selected to apply an appropriate weighing to the idealized face vector elements of the target standard population vector so to correspondingly favour certain standard face vector elements over others in favouring the particular preferences of the intended audience of interest. In one embodiment, the elements of the audience vector are equal to the multiple regression coefficients of a multiple regression with the elements of the face vectors of the sample faces as predictors and the attractiveness ratings as predictions.

EXAMPLE

Figure 4:
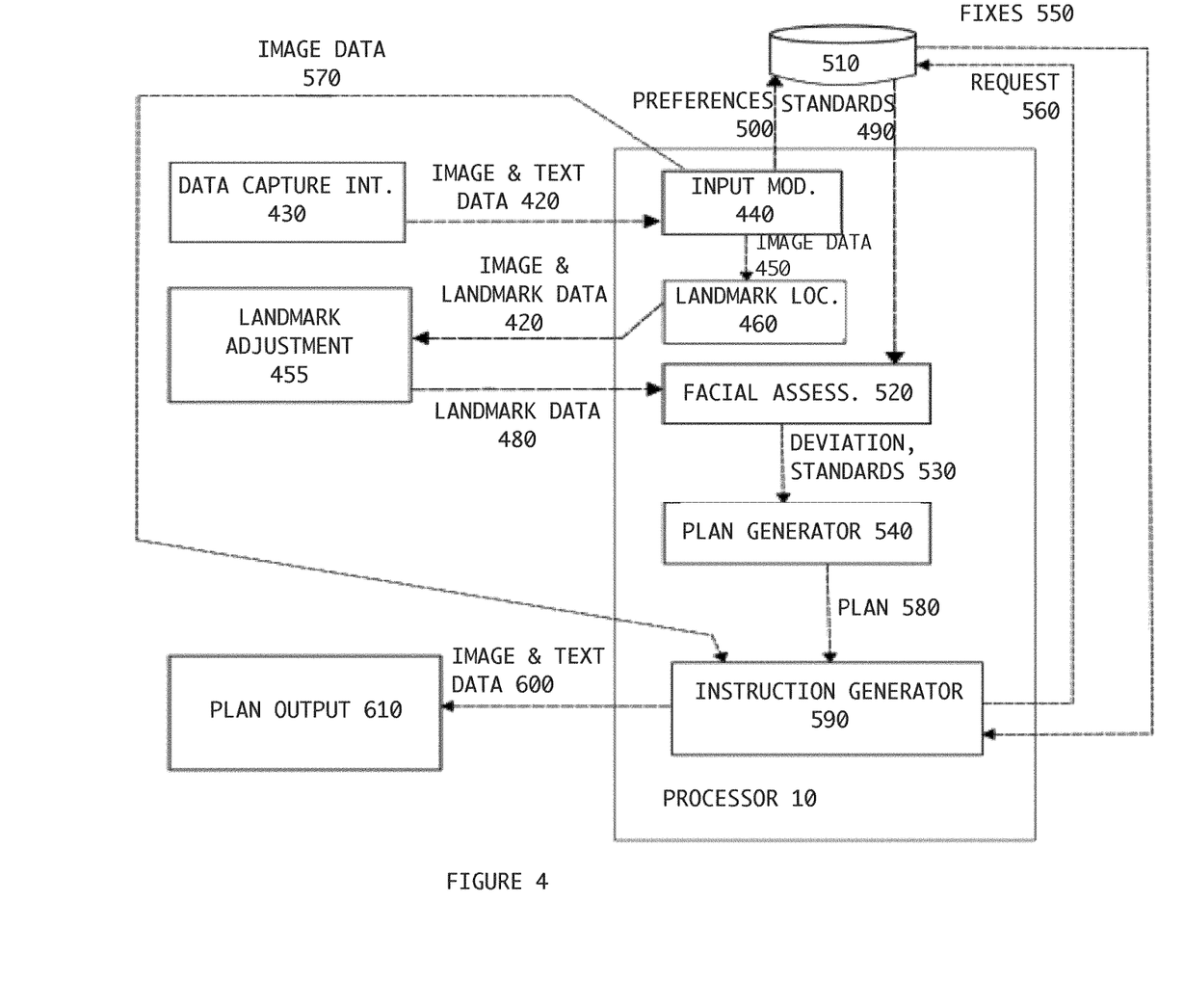
FIG. 4 is a schematic diagram of an exemplary system data flow for automatically generating a facial remediation design and application protocol to address facial deviations, in accordance with one embodiment.

The following describes one exemplary embodiment of a facial remediation design and protocol generation method and system, as described above. In this example, a system, generally illustrated at FIG. 4, is provided to automatically generate a remediation plan output 610 for each given user that will change the appearance of this user's face such that their appearance is closer to that defined by one or more standard facial structure and/or audience facial characteristic datasets chosen by and/or for this user.

Generally, the system will first require execution of a standardization process whereby a system database 510 of preset standards 490 can be built and populated by a local, shared or network processor 410 to provide comparative bases for the assessment of user appearance deviations from a selected or preset ideal(s), and the generation of a remediation design and protocol to at least partially address such deviations. In this illustrative example, the system dataset is populated as follows.

A collection of sample facial images are first collected from one or more target population demographics to form respective target population-specific Standards, each group represented by a number of persons of a particular gender, age range, ethnic origin and the like. Each standard population will generally be represented by a large sample of facial images forming a set M of such facial images. On the basis of this sample set of images, a corresponding set of facial structures may be defined and compiled for each sample in each set M. For example, in one embodiment, an image processing module can be used to automatically locate facial landmarks on each image, optionally including a series of randomly oriented facial images, and determine corresponding facial structures as face vectors to and/or between such landmarks. In some implementations, a user interface may be provided to allow a user to adjust a location of automatically identified landmarks (i.e. adjust the positions of misplaced landmarks) so to optimize an accuracy of generated structural face vectors. In other embodiments, a user may manually identify certain facial landmarks via this interface for subsequent processing of corresponding facial vectors.

Once each sample in a given set M have been processed, a random audience can be selected to assess an attractiveness of each sample image and assign a corresponding attractiveness rating thereto for further processing. From compiled audience ratings, an overall attractiveness score can be defined for each facial image sample in the set. In one embodiment, this score is defined as H(R), where R is the set of attractiveness ratings assigned to a particular image by the random audience, and where $$H(R) = \frac{\sum_{i=1}^{n} r_i}{n}$$

where n is the number of raters and $r_i$ is the rating given to a particular face by the $i^{th}$ rater. The overall attractiveness score can then be used to select a subset of the samples in M to define idealized Standard structural features for this set. As will be appreciated by the skilled artisan, the number of samples in this subset may vary depending on the intended results, ranging from one or a few idealized target samples, in which case the attractiveness score may play a particularly significant role, to the entire set when seeking to generate an average or generic population ideal for which the attractiveness scores may play a minimal effect. Accordingly, the subset may be defined by an attractiveness threshold or again a preset subset number of required samples, or alternatively rely on a weighted or otherwise relative impact scale to apply greater importance to those samples having received a higher overall attractiveness score.

In this particular example, a subset of the highest scoring sample images in M are used to form the structural facial Standards for the given population defined for this set, each structural elements of which, in one embodiment, being defined as $G(S_i')$ where $S_i'$ is the $i^{th}$ element of the facial structures defined for each face in M. In this particular example, $G(S_1')$ is taken as the average value of $S_i'$ over the entire subset, which can otherwise be expressed as $$G(S_i') = \frac{\sum_{k=1}^{n} r_{ik}}{n}$$

where $S_i'$ is the set of the $i^{th}$ elements of the facial structures of the most attractive faces in M, and k is the $k^{th}$ element of the $S_i'$ Face Vector.

In yet another example, one or more Audience-specific preferences may be identified to calibrate an impact or relative importance different facial structures may have on the selection of structural features to favour in defining a particular Standard, which may result in an expanded set of Audience-specific, weighted or influenced Standards. A user may thus later identify with one or more of these audience preferences in customizing facial features, appearances and/or styles to be predominantly addressed in designing a remediation output protocol for this user. Accordingly, different idealized facial structure sets may be characterized for a same sample set based on different Audience characteristics. In doing so, the system may automatically compute and associate an Audience characteristic with the images in the set M by calculating the relative importance of each element of the facial structure in determining the attractiveness score for each of the sampled faces. Such relative values may be the coefficients of a multiple regression analysis, for example, with the elements of the facial structure as the predictors and the attractiveness ranking as the prediction. For example, in one embodiment, the relative importance of each structural element of a given Standard can be calculated as $\gamma(\beta,\alpha)$, where $\gamma(\beta,\alpha)$ is a multiple regression with $\beta$, the set of facial structures of the elements of M, as predictors and $\alpha$, the attractiveness ratings of the elements of M, as the predictions, to form a set $\varphi$ of Audience characteristics which may be expressed as an Audience Vector whose elements are the coefficients from $\gamma(\beta,\alpha)$.

With the system's population-specific idealized attractiveness face structure standards and optional audience-influenced preferences computed and stored, the system may be operated to automatically assess user images to identify deviations from such Standard structures and/or Audience preferences, and generate a proposed remediation design and protocol to address such identified deviations to better align the user's facial appearance with the selected standard and/or preference(s).

As introduced above, a suitable image of the subject's face, as well as a selected standard, optional style and/or preferred audience is received as input 420 to input module 440, for instance in part, directly or indirectly relayed from an integrated or interfacing data capture interface 430. User options may include, but are not limited to, a selected standard population, audience and optional makeup style, as well as various optional user preference options which may include searching and selecting one or more known facial structures (e.g. celebrities, politicians, athletes, etc.) to find a celebrity or celebrities with the closest matching facial structure to the user. This search and identification may be executed manually by the user and/or subject, or again implemented automatically to issue recommendations to the user for consideration. Upon selection of a given one or more celebrity structure as basis or influence on the standard structure of interest, the subject's output remediation design and protocol may yield a resulting appearance similar to that selected celebrity.

Image data 450 is then relayed to a landmark location module 460 such that the facial structures of the acquired image can be determined, for example as described above for the sample image set(s), and stored for comparative purposes. Again, a landmark adjustment interface 455 may be provided to allow a user to adjust a location of the automatically identified landmarks 420 so to output optimized structural landmark data 480 to be processed by the facial assessment module 520.

In one example, the facial assessment module 520 is executed to determine the difference between the user's facial structure and the standard structure of interest, the particulars of which are accessed from the database 510. For example, one or more deviation vectors D can be defined in which the $i^{th}$ element, $d_i$, is calculated to define a particular user deviation from a corresponding element of the selected Standard. For example a deviation vector may be defined as a one dimensional vector whose elements $d_i$ are formed by F(S,U), where S is a Standard vector and U is a user vector, and defined as:

$$d_i = \frac{S_i - U_i}{S_i} \tag{1}$$

where $d_i$ is the $i^{th}$ element of the deviation vector, $S_i$ is the value of the $i^{th}$ element of the Standard vector, and $u_i$ is the value of the $i^{th}$ element of the user vector, for example. Alternatively, a standard deviation vector may be defined as a one dimensional vector whose elements $t_i$ are rather formed by calculating the standard deviations of the elements of the face vectors of those members of the Standard population selected to form the Standard Vector, and defined as:

$$t_i = \frac{S_i - U_i}{\sigma_i} \tag{2}$$

where $t_i$ is the $i^{th}$ element of the user-to-standard deviation vector D (hereinafter referred to as the standard deviation vector), $S_i$ is the value of the $i^{th}$ element of the Standard vector, $u_i$ is the $i^{th}$ element of the user vector and $\sigma_1$ is the $i^{th}$ element of the standard base set standard deviation vector, for example.

Additional or alternative facial assessments may include, but are not limited to, the computation of a Horizontal Paired Asymmetry Vector (i.e. defined as a one dimensional vector whose elements are formed by calculating the ratio of the distance from each element of each symmetrical pair to the vertical centre line to the distance from the nasion to the Gnathion or another pair of landmarks), a Vertical Paired Asymmetry Vector (i.e. defined as a one dimensional vector whose elements are formed by calculating ratio of the vertical distance between each element of the symmetrical pair and the distance from the nasion to the Gnathion or another pair of landmarks), and Centre Line Asymmetry Vector (i.e. defined as a one dimensional vector whose elements are formed by calculating the ratio of the horizontal displacement from the Vertical Centre line of landmarks which should naturally fall on the Vertical Centre Line, for example the nasion and the pronasion, to the distance from the nasion to the Gnathion or another pair of landmarks), for example.

Once the user's various structural deviations 530 have been computed and stored, these can be relayed to a facial remediation plan generator 540 along with the selected standard to invoke the automatic construction of an appropriate facial remediation plan 580 that will at least partially address some of these deviations to render the user's appearance as close as possible to the selected Standard. In the following example, the corrections are annotated as the set L(D, $\varphi$), where D is the set of computed deviations from Standard and $\varphi$ is the optional Audience-specific characteristic(s) selected by the user, described above.

To compute the structural corrections, the elements $d_i$ of deviation vector D are ordered based on the deviation order values $o_i$ calculated by applying one of the following equations:

$$o_i = a_i e^{|d_i|} \quad (3)$$

where $o_i$ is the order of the $i^{th}$ deviation, $a_i$ is the multiple regression coefficient of the $i^{th}$ deviation, $d_i$ is the $i^{th}$ element of the deviation vector D as calculated using equation (1); or $$o_i = a_i e^{|t_i|} \quad (4)$$

where $O_i$ is the order of the $i^{th}$ deviation, $a_i$ is the multiple regression coefficient of the $i^{th}$ deviation, $t_i$ is the $i^{th}$ element of the Deviations Vector D as calculated using equation (2); or $$O_i = \frac{a_i}{\sigma_i \sqrt{2\pi}} \left(1 - e^{-\frac{(s_i - u_i)^2}{2\sigma_i^2}}\right) \quad (5)$$

where $O_1$ is the order of the ith deviation, $a_i$ is the multiple regression coefficient of the $i^{th}$ deviation, $s_i$ is the value of the $i^{th}$ element of the Standard vector, $u_i$ is the $i^{th}$ element of the user vector and $\sigma_i$ is the $i^{th}$ element of the standard base set standard deviation vector.

In yet other embodiments, the system may also invoke computed asymmetry vectors by ordering both the elements of the deviations vector and of the asymmetry vectors by the value of $O(d_i, v_i)$, much as considered above in Equations 3 to 5, where $d_i$ is the $i^{th}$ element deviations vector and $v_i$ is the set of $i^{th}$ elements of the asymmetry vectors.

Once the deviations and/or asymmetries have been ordered as detailed above, a subset of these deviations can be selected to propose appropriate facial remediation fixes that may be helpful in addressing these selected deviations. In other words, the system will automatically customize its output to address the highest ranking deviations first, that is to instruct application of facial remediation fixes in proportion to the degree of the corresponding deviation or asymmetry, so to direct the greatest impact on the user's facial appearance in bringing it closer into line with the selected standard, and optional audience. Namely, the proposed remediation fixes will have the effect of actually or effectively visually shifting the location or size of an anatomical feature of the subject's face (e.g. eye, chin, cheekbone, etc.) so to better align with the selected standard and/or audience.

In one particular embodiment, the system implements a non-surjective, non-injective mapping of the ordered deviations and asymmetries onto remediation fixes such that the application of the remediation fixes mapped from a particular deviation or asymmetry will reduce the actual deviation or the appearance of this deviation or asymmetry. In doing so, the system's remediation applicator and instruction generator 590 effectively requests (560) appropriate preset remediation fixes 550 stored in database 510 that can at least partially address the processed deviations 530 from the idealized standard, and in this example output (600) both a structured set of written instructions to guide the application of remediation fixes and an enhanced rendition of the user's original image to show the impact the proposed remediation design and protocol should have on the user's overall facial appearance 610. For instance, the facial remediation applicator and instruction generator 590 can automatically alter the user's facial image so as to incorporate a facial remediation plan in order to show the user the result of applying the makeup plan to his or her face, along with a list of instructions for applying the facial remediation plan.

In one particular embodiment, the user's image is altered by digitally stretching the output makeup fixes 550 to match the structure of the subject's face and then sequentially combining each of the stretched makeup fixes with the subject's image to render the final image 600 in the output 610. Accordingly, the resulting facial image may have the same underlying structure as the subject's face while exhibiting a resulting colouration defined by the combination of the colourations of the makeup fixes. This approach may thus allow the system to construct an image of the subject's face with the makeup fixes applied to the image such as to demonstrate the effect of the makeup plan on the subject's appearance as the user evaluates the output and learns how to implement the output design and protocol.

In some embodiments, the proposed makeup fixes may include several degrees of intensity, which may, for example, permit a graduated application of a makeup effect as the subject transitions its appearance accordingly.

While the present disclosure describes various exemplary embodiments, the disclosure is not so limited. To the contrary, the disclosure is intended to cover various modifications and equivalent arrangements included within the general scope of the present disclosure.

What is claimed is:

1. A computerized method for automatically developing a facial remediation protocol for a user based on an input facial image of the user, the method comprising:
    defining a digital user facial structure of the user based on the input facial image;
    retrieving a designated digital standard facial structure from accessible data storage;
    computing structural deviations between said digital user facial structure and said designated standard facial structure;
    retrieving preset digital facial remediation protocol fixes corresponding to at least some of said computed deviations from said accessible data storage, wherein one or more preset facial remediation protocol fixes have been pre-established to at least partially reduce a visual appearance of corresponding structural deviations; and
    outputting a digital remediation protocol according to said preset digital facial remediation protocol fixes,
    wherein said defining said digital user facial structure comprises automatically identifying a user set of preset structural landmarks from the input facial image and defining a digital user landmark representation thereof, said designated digital standard facial structure comprises a corresponding standard landmark representation of a corresponding standard set of preset structural landmarks, and said computing comprises computing deviations between said user landmark representation and said standard landmark representation.

2. The method of claim 1, wherein said user landmark representation is defined by a user vector of constituent user landmark ratios and wherein said standard landmark representation is defined by a standard vector of constituent standard landmark ratios.

3. The method of claim 2, wherein said deviations are represented by a deviation vector.

4. The method of claim 3, wherein said deviations are further represented by an asymmetry vector representative of computed asymmetries identified from said user facial structure.

5. The method of any one of claims 1, 2, 3, and 4, wherein said structural deviations are automatically ordered, and wherein said preset digital facial remediation protocol fixes are retrieved so as to address a highest ordered subset of said deviations.

6. The method of anyone of claim 1, wherein said standard facial structure is selectable to correspond with one or more user demographical characteristics.

7. The method of claim 6, wherein said one or more user demographical characteristics include at least one of a user age, a user age range, a user ethnicity, and a user gender.

8. The method of claim 6, wherein said standard facial structure is defined as a function of a set of sample facial images of individuals satisfying said one or more demographical characteristics.

9. The method of claim 8, wherein said standard facial structure is defined as a function of an average representation of one or more standard landmarks extracted from each of said set of sample images.

10. The method of claim 8, wherein said facial structure is defined as a function of an attractiveness rating associated with each of said set of sample facial images.

11. The method of claim 8, further comprising receiving as input a selected audience, wherein an audience-specific weighing is applied against said one or more standard landmarks in defining an audience-specific standard facial structure to preferentially appeal to said selected audience.

12. The method of claim 1, wherein said outputting comprises digitally enhancing the facial image to apply said digital facial remediation protocol thereto and output an enhanced digital image representative thereof.

13. The method of claim 12, wherein said enhanced digital image includes an ordered set of enhanced digital images illustrating a series of steps in a progressive application of said digital facial remediation protocol.

14. The method of claim 1, wherein said outputting comprises ordered written instruction for implementing said digital facial remediation protocol.

15. The method of claim 12, wherein an intensity of one or more proposed makeup fixes of said digital facial remediation protocol is adjustable.

16. The method of claim 1, wherein the image is one of a 2D image and a 3D image.

17. The method of claim 1, wherein said facial remediation protocol consists of a makeup application protocol.

18. A computer-readable medium having statements and instructions stored therein for implementation by a hardware processor to implement the steps of claim 1.

19. A computerized system for automatically developing a facial remediation protocol for a user based on an input facial image of the user, the system comprising:
    an image input interface;
    a facial remediation protocol output interface;
    a hardware processor; and
    a data storage device having stored thereon:
    a set of selectable digital standard facial structures;
    a set of preset digital facial remediation protocol fixes pre-established to at least partially adjust a visual appearance of corresponding facial landmarks or representations thereof; and
    statements and instructions for execution by said hardware processor to:
        define a digital user facial structure of the user based on the input facial image received as said image input interface;
        retrieve a designated one of said selectable standard facial structures;
        compute structural deviations between said digital user facial structure and said designated one of said standard facial structures;
        compile a subset of said set of preset digital facial remediation protocol fixes corresponding to at least some of said computed deviations as an output digital makeup protocol; and
        output said digital facial remediation protocol to said output interface,
    wherein said input interface and said output interface each comprise a network accessible interface, and wherein the system is configured to receive, over a communication network, the input facial image of the user via said input interface, and retrieve, over the communication network, said output digital makeup protocol from said output interface.

20. The system of claim 19, further comprising an image capture device operatively coupled to said input interface.

21. A computerized system for automatically developing a facial remediation protocol for a user based on an input facial image of the user, the system comprising:
    an image input interface;
    a facial remediation protocol output interface;
    a hardware processor; and
    a data storage device having stored thereon statements and instructions for execution by said hardware processor to implement the steps of claim 1.

22. A computerized method for automatically developing a facial remediation protocol for a user based on an input facial image of the user, the method comprising:
    defining a digital user facial structure of the user based on the input facial image;
    retrieving a designated digital standard facial structure from accessible data storage;
    computing structural deviations between said digital user facial structure and said designated standard facial structure;
    retrieving preset digital facial remediation protocol fixes corresponding to at least some of said computed deviations from said accessible data storage, wherein one or more preset facial remediation protocol fixes have been pre-established to at least partially reduce a visual appearance of corresponding structural deviations; and
    outputting a digital remediation protocol according to said preset digital facial remediation protocol fixes,
    wherein said outputting comprises digitally enhancing the facial image to apply said digital facial remediation protocol thereto and output an enhanced digital image representative thereof, and
    wherein said enhanced digital image includes an ordered set of enhanced digital images illustrating a series of steps in a progressive application of said digital facial remediation protocol.

23. The method of claim 22, wherein said outputting comprises ordered written instruction for implementing said digital facial remediation protocol.

24. The method of claim 22, wherein an intensity of one or more proposed makeup fixes of said digital facial remediation protocol is adjustable.

* * * * *